United States Patent
Pfeiler

(10) Patent No.: US 8,280,490 B2
(45) Date of Patent: Oct. 2, 2012

(54) REGISTRATION AID FOR MEDICAL IMAGES

(75) Inventor: Manfred Pfeiler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 2067 days.

(21) Appl. No.: 11/292,960

(22) Filed: Dec. 2, 2005

(65) Prior Publication Data

US 2006/0184014 A1  Aug. 17, 2006

(30) Foreign Application Priority Data

Dec. 2, 2004  (DE) .......................... 10 2004 058 122

(51) Int. Cl.
*A61B 5/00* (2006.01)

(52) U.S. Cl. ........................................ 600/426; 600/429

(58) Field of Classification Search .......... 600/407–410, 600/424–429; 381/329; 378/164, 206; 356/247, 356/248

See application file for complete search history.

(56) References Cited

U.S. PATENT DOCUMENTS

| | | | |
|---|---|---|---|
| 4,860,331 A * | 8/1989 | Williams et al. ............... 378/163 |
| 4,957,124 A * | 9/1990 | Mooney ........................ 132/200 |
| 5,368,030 A * | 11/1994 | Zinreich et al. ............... 600/414 |
| 5,383,454 A * | 1/1995 | Bucholz ........................ 600/429 |
| 5,445,608 A * | 8/1995 | Chen et al. ..................... 604/20 |
| 5,588,430 A * | 12/1996 | Bova et al. .................... 600/429 |
| 5,594,786 A * | 1/1997 | Chaco et al. ............... 379/93.09 |
| 5,676,673 A * | 10/1997 | Ferre et al. .................... 606/130 |
| RE35,816 E * | 6/1998 | Schulz ........................... 356/608 |
| 5,765,561 A * | 6/1998 | Chen et al. ..................... 600/407 |
| 5,769,861 A * | 6/1998 | Vilsmeier ...................... 606/130 |
| 5,782,765 A * | 7/1998 | Jonkman ........................ 600/424 |
| 5,813,984 A * | 9/1998 | Haaga et al. .................. 600/410 |
| 5,827,186 A * | 10/1998 | Chen et al. ..................... 600/407 |
| 5,836,954 A * | 11/1998 | Heilbrun et al. .............. 606/130 |
| 5,873,822 A * | 2/1999 | Ferre et al. ..................... 600/407 |
| 5,891,034 A * | 4/1999 | Bucholz ........................ 600/426 |
| 5,954,647 A * | 9/1999 | Bova et al. ..................... 600/407 |
| 5,967,980 A * | 10/1999 | Ferre et al. ..................... 600/424 |
| 6,006,126 A * | 12/1999 | Cosman ........................ 600/426 |
| 6,122,541 A * | 9/2000 | Cosman et al. ............... 600/426 |
| 6,127,672 A * | 10/2000 | Danisch ..................... 250/227.14 |

(Continued)

OTHER PUBLICATIONS

"A Survey of Medical Image Registration," Maintz et al, Medical Image Analysis (1998), vol. 2, No. 1, pp. 1-36.

(Continued)

*Primary Examiner* — Sanjay Cattungal
(74) *Attorney, Agent, or Firm* — Schiff Hardin LLP

(57) ABSTRACT

A registration aid for medical images obtained from an examination subject respectively with different imaging modalities at separated points in time, has a carrier adapted to be reproducibly applied to an examination subject at separated points in time at a substantially identical position on the examination subject at each of the separated points in time, and at least one landmark provider carried by the carrier, the landmark provider providing a first landmark visible in a first of the imaging modalities and a second landmark, different from the first landmark, visible in a second of the imaging modalities. The landmark provider provides the first and second landmarks with a fixed spatial relation relative to each other to allow contents of an image obtained with the first of the imaging modalities to be brought into registration with contents of an image obtained with the second of the imaging modalities, with the carrier being applied to the examination subject while each of the images is obtained.

12 Claims, 3 Drawing Sheets

U.S. PATENT DOCUMENTS

| | | |
|---|---|---|
| 6,246,900 B1 * | 6/2001 | Cosman et al. ............... 600/426 |
| 6,259,355 B1 * | 7/2001 | Chaco et al. ............. 340/286.07 |
| 6,259,942 B1 * | 7/2001 | Westermann et al. ........ 600/426 |
| 6,272,370 B1 * | 8/2001 | Gillies et al. ................... 600/411 |
| 6,273,896 B1 * | 8/2001 | Franck et al. ................. 606/130 |
| 6,275,725 B1 * | 8/2001 | Cosman ........................ 600/426 |
| 6,282,437 B1 * | 8/2001 | Franck et al. ................. 600/429 |
| 6,298,262 B1 * | 10/2001 | Franck et al. ................. 600/426 |
| 6,341,231 B1 * | 1/2002 | Ferre et al. .................... 600/424 |
| 6,348,058 B1 * | 2/2002 | Melkent et al. ............... 606/130 |
| 6,351,662 B1 * | 2/2002 | Franck et al. ................. 600/429 |
| 6,402,762 B2 * | 6/2002 | Hunter et al. ................. 606/130 |
| 6,445,943 B1 * | 9/2002 | Ferre et al. .................... 600/424 |
| 6,491,699 B1 * | 12/2002 | Henderson et al. ........... 606/130 |
| 6,529,765 B1 * | 3/2003 | Franck et al. ................. 600/427 |
| 6,546,277 B1 * | 4/2003 | Franck et al. ................. 600/426 |
| 6,675,040 B1 * | 1/2004 | Cosman ........................ 600/427 |
| 6,697,664 B2 * | 2/2004 | Kienzle, III et al. .......... 600/427 |
| 6,738,656 B1 * | 5/2004 | Ferre et al. .................... 600/426 |
| 6,782,287 B2 * | 8/2004 | Grzeszczuk et al. .......... 600/424 |
| 6,837,864 B1 * | 1/2005 | Bertolero et al. ............ 604/6.16 |
| 6,926,673 B2 * | 8/2005 | Roberts et al. ................ 600/464 |
| 7,117,027 B2 * | 10/2006 | Zheng et al. .................. 600/426 |
| 7,200,251 B2 * | 4/2007 | Joshi et al. .................... 382/128 |
| 7,483,049 B2 * | 1/2009 | Aman et al. .................. 348/162 |
| 7,869,861 B2 * | 1/2011 | Moctezuma de la Barrera et al. ............................. 600/426 |
| 2001/0016684 A1 * | 8/2001 | Shahidi ........................ 600/429 |
| 2001/0027271 A1 * | 10/2001 | Franck et al. ................. 600/426 |
| 2002/0077543 A1 * | 6/2002 | Grzeszczuk et al. .......... 600/424 |
| 2002/0087101 A1 * | 7/2002 | Barrick et al. ................ 600/587 |
| 2002/0147455 A1 * | 10/2002 | Carson ......................... 606/130 |
| 2002/0188194 A1 * | 12/2002 | Cosman ........................ 600/426 |
| 2002/0198451 A1 * | 12/2002 | Carson ......................... 600/424 |
| 2003/0069591 A1 * | 4/2003 | Carson et al. ................. 606/130 |
| 2003/0095186 A1 * | 5/2003 | Aman et al. .................. 348/162 |
| 2003/0120283 A1 * | 6/2003 | Stoianovici et al. .......... 606/130 |
| 2003/0130610 A1 * | 7/2003 | Mager et al. ................ 604/6.16 |
| 2003/0159141 A1 * | 8/2003 | Zacharias ....................... 725/37 |
| 2006/0064030 A1 * | 3/2006 | Cosentino et al. ............ 600/547 |
| 2006/0089626 A1 * | 4/2006 | Vlegele et al. .................... 606/1 |
| 2009/0046152 A1 * | 2/2009 | Aman ........................... 348/157 |
| 2011/0077510 A1 * | 3/2011 | Moctezuma de la Barrera et al. ............................. 600/426 |

OTHER PUBLICATIONS

"SPECT and CT Kombiniert," Downer, Medical Solutions, Nov. 2004, pp. 16-21.

* cited by examiner

REGISTRATION AID FOR MEDICAL IMAGES

BACKGROUND OF THE INVENTION

1. Field of the Invention

The present invention concerns a registration aid for medical images, and in particular, a registration aid that is applied to (worn by) a patient from whom medical images are obtained with two different imaging modalities at separated points in time, that allows the contains of the respective images to be brought into registration with each other.

2. Description of the Prior Art

Up to the beginning of the 1970s, medical diagnostic imaging was the domain of classical x-ray technology with projection images. Ultrasound imaging as well as the imaging of nuclear medicine were still at the beginning of their development. X-ray computed tomography (CT) arrived in the seventies, magnetic resonance tomography (MRT) in the eighties. CT and MRT provide cross-section images that show different properties of the examined tissue. CT shows the properties of the spatially-dependent x-ray radiation attenuation of the examined tissue, MRT shows properties that relate to the nuclear spin of the atoms in the tissue, primary hydrogen atoms. Nuclear medical imaging has also been further developed in the direction of the cross-section image representation in parallel with the development of CT and MRT. Imaging by measurement of the intensity of gamma radiation or of photons that emanate from tissue locations in which material specifically emitting this type of radiation was enriched by means of an applied radio pharmaceutical is an example (SPECT=single photon emission computerized tomography). Another nuclear-medical method is PET (position emission tomography), in which a positron-emitting material is administered in a comparable manner to tissue locations, and the emitted positrons combine with an electron in the immediate proximity of their emission locations and thus generate gamma radiation. Imaging with ultrasound has also made significant advances.

The aforementioned non-nuclear medical methods all address different tissue properties or the same tissue properties but with different sensitivity, specificity and the type of the representation. Depending on the problem at hand, a specific method is advantageously applied; for specific problems the application of multiple methods can also decisively increase the diagnostic information.

Nuclear medicine images (SPECT, PET) show intensity distributions in the tissue cross-section mapped in them. These intensity distributions (depending on the composition of the radio pharmaceutical) can represent healthy or normally-functioning tissue (such as, for example, the heart muscle) based on its metabolism or can indicate pathological tissue (such as carcinoma metastases in the liver or in bones) based on a pathological metabolism. Clearly-shown structures are absent or only poorly indicated in non-nuclear medical images, such that a metabolically-active tissue shown by an intensity distribution cannot be classified or can only be insufficiently classified in the morphology of the body cross-section. For specific diagnostic questions, it would be of particular advantage to know the precise location of an intensity distribution within an organ, that could be visualized as if the nuclear-medical slice image and the non-nuclear medical slice image were brought into registration. The purpose of the image registration is to transform the locations of the same tissue or organ points of the body or tissue cross-section, shown in both imaging types or image modalities, such that they have the same spatial coordinates in a common spatial coordinate system or that, in this sense, such locations in the coordinate system of the one modality are even transformed into the coordinate system of the other modality. Such a transformation generally is not achieved solely with a rotation and/or displacement because it is to be assumed that the border of the body cross-section in the image, like the shown organs, is shown differently in the image acquisition processes with both modalities, even when the image section is at the same level in the patient positioning (for example by displacement of inner organs). The registration here is a difficult process.

The process of merging of both images for "integrated display" of both image contents follows the process of the registration. This process of merging is designated as image fusion. This occurs by superimposition of both (registered) images, and for better differentiation of the different content, for example, the nuclear-medical image is applied in color and thus is overlaid on the black-and-white CT image. Since here images of different modalities are registered and merged, this can be considered as a multimodal registration and fusion, but because two modalities are involved, it is more accurate to use the term bimodal registration and fusion.

This process and its fundamental importance are explained using FIG. 1 and FIG. 2, wherein for the selected example the ideal case is assumed that, in the transition from the generation of the Ct image according to FIG. 1a to the acquisition of the PET image according to FIG. 1b, the patient cross-section has experienced no change, for example due to organ displacement or even due to different positioning. FIG. 1a shows a cross-section 1 at the body trunk in a highly schematized manner, with the representation of the liver 2, the aorta 3, the spinal column 4 and both kidneys 5 and 6. The structures that are not further designated represent lung tissue (the large, dark checkered area), the ribs and parts of the digestive system located in the cross-section. The structure 8 represents the pancreas, in which a radiologist should diagnose a cancer source due to its shape and its structure. The expansion of the this source should now be established with a PET exposure and, most notably, the question should be answered of whether the source is limited to the pancreas or is drawing into the stomach artery 7 which (according to FIG. 1a) abuts the aorta 2 on one side and the pancreas 8 at another.

The PET image for the same patient cross-section is shown in FIG. 1b with the radioactive region 9 in an area that is to be associated with the pancreas, and both radioactive regions 10 and 11 that are obviously located in the border areas of the kidneys and which may occur here due to the elimination process for the radio-pharmaceutical proceeding through the kidneys.

If the PET image according to FIG. 1b is successfully superimposed ("fusion") on the CT image according to FIG. 1a by ensuring the same imaging scales and the same spatial image orientation ("registration") in a spatially-accurate manner, the fused image is obtained as shown in FIG. 1c. In the example (lacking color representation in the drawings) in the FIG. 1c, the tonal value "white" was associated with the region 9' that corresponds to the radioactive region 9 in FIG. 1b; the kidney portions characterized as radioactive in FIG. 1b, namely the regions 10 and 11 in FIG. 1c, were also adopted with similar characterization as the regions 10' and 11' (also in order to indicate the spatially-correct superimposition).

In this example, the result of the image fusion is not be just that the cancer diagnosis according to the CT image was confirmed by the PET examination, but rather also that the extent of the source is shown with the important visualization that the source transgresses the organ boundaries of the pancreas 8 and encroaches into the stomach artery 7.

The example using FIG. 1a through FIG. 1c applies in a practically identical manner for the imaging type SPECT in place of that of PET. The same would apply if MRT took the place of CT. In principle, other imaging types could also be combined with one another, for example CT and ultrasound. In the case of a combination of different imaging types, multimodal image registration and fusion are referred to in contrast to monomodal (where, for example, images of the same imaging type that were acquired at different points in time are fused with one another in order, for example, to monitor the course of a treatment).

A comprehensive overview of image registration is found in the article "A Survey of Medical Image Registration" by J. B. A. Maintz and M. A. Viergever in Medical Image Analysis, Oxford University Press 1998.

Another example for monomodal image registration and fusion is now discussed. The object is to reliably track a disease or healing progress with by means of CT for soft tissue disease in the skull. In a reference exposure showing the initial situation, the image window (or, more accurately, the signal level window) is selected such that exclusively or predominantly the cranial bone is shown. With successive exposures after specified time periods or after procedures, the cranial bone is initially shown with the same image window and is brought into registration (by image rotation or displacement) with the reference image selected earlier. The image window is then adjusted such that critical soft tissue changes can be detected in the best possible manner. For example, a subtraction of both images to produce a different image that shows the changes that have occurred in the meantime can then be helpful for the comparison.

The above discussion did not take into account the problem that a tilting of the patient's head with regard to his longitudinal axis thereof in successive acquisitions is not always preventable even with diligent efforts. "Landmarks" or "landmark providers" appearing in the image that remain fixed on the skull of the patient over the duration of the monitoring examinations (for example by screws in the bones) provided a solution. This ensures that only identical skull cross-sections (namely characterized by the same occurrence of the landmarks in the images) are compared.

Registration is also difficult in a monomodal case when a body cross-section must be examined in successive image that has no fixed frame such as the cranial bone for the skull. CT images acquired at different times, even of an identical cross-section of the body trunk, are different when (for example as mentioned above in the body trunk example for multimodal registration), the shown organs and the border of the body cross-section appear different in the images due to the displacement of inner organs in the images. A rigid reference system inherent to the body is not present, on which reference system landmark providers could be applied that could be found again in the image. The registration thus must be based on the shown tissue or organ structures, a process that becomes more complex the farther apart in time the different examinations of the patient are from one another.

The registration is more difficult in the multimodal (more precisely stated, bimodal) case, for example of CT and PET, as was also already recognizable in the example discussed using FIG. 1a through 1c.

Under the assumption that, in the example according to FIG. 1, organ displacements would have occurred in the transition from the examination according to the image in FIG. 1a with CT to the nuclear-medical examination according to the image in FIG. 1b, instead of the PET image shown in FIG. 1b one such as in FIG. 1d could be prepared. The active regions 9, 10 and 11 shown in FIG. 1b are found again in FIG. 1d as the regions 9", 10" and 11". The body cross-section 1 according to FIG. 1a, characterized in FIG. 1b as body cross-section 1', has changed in terms of its shape in connection with the organ displacement, as indicated in FIG. 1d as body cross-section 1". For clarification, parts of the contours of the radioactive regions 9, 10 and 11 shown in FIG. 1b are plotted in equivalence in FIG. 1d as 9\*, 10\* and 11\*.

It can now be attempted to stretch, compress, rotate and displace the image in FIG. 1d in specific image ranges by means of image processing until the kidney contours 10" and 11" indicated by the activities come into congruence with the fully-formed contours of the kidneys 5 and 6 in FIG. 1a. However, the question then always exists as to whether, due to this transformation, the topology of the image in FIG. 1d entirely or approximately coincides with that which was displayed in the image in FIG. 1a if it were to be "inherently visible" or, expressed otherwise, whether it coincides with that which was introduced by FIG. 1b into the image of FIG. 1a as area 9 and then appears in FIG. 1c as region 9'. It is still true that the advantageous possibility to effect an adaptation of the body cross-section 1" in FIG. 1d to the body cross-section 1 in the image of FIG. 1a is not available, because even the body cross-section 1" in the PET image according to FIG. 1d (and that characterized in the image of FIG. 1b and here as 1') is not mapped or is less sufficiently mapped.

An algorithm that can be considered as applying a rubber blanket onto the image in FIG. 1d traces the radioactive area 9" and the kidney contours indicated in the active radiation regions 10" and 11" onto the rubber blanket, if applicable after clarification of the kidney contours by an experienced doctor. Such an algorithm would have to rotate this rubber blanket (for example by spatially-dependent dragging) so as to rotate or to shift it as a whole, or only for local image parts (and decreasingly at their boundary regions) until the kidney contours shown (and, if applicable, clarified by manipulation) in FIG. 1d with the regions 10" and 11" coincide with those shown in FIG. 1a. Given the development of such an algorithm, it would be necessary to incorporate prior information into it that displace it in terms of position to take into account possible preferential directions in which, for example, the pancreas displaces when one or both kidneys 5 and 6 are shifted in the direction of the inside of the body by displacement of the patient.

An image fusion of CT images and PET images is today is viewed as so important for diagnostics but their correct registration is viewed as so difficult that the mathematical process of a complex image transformation is circumvented by a physical solution. This is to combine CT and PET in one apparatus, such only a displacement of the patient positioning table is needed to transport the patients from one into the other acquisition mode; a repositioning of the patient thus is not done. The acquisitions of the different types are executed in one examination step, one immediately after the other, such that an inherent movement of the organs (for example due to intestinal peristalsis) can also be assumed as not present or as only slight. It is assumed that the cross-section images of both modalities CT and PET incorporated in one apparatus are of practically identical topology.

Combined CT/PET systems are already commercially available; a serially-produced CT/SPECT apparatus was introduced in the middle of 2004 (Medical Solutions including electromedica, November 2004, page 16). The previously employed and continuing observations for a CT/PET apparatus equally apply for a CT/SPECT apparatus.

Such a CT/PET apparatus, however, does not solve the registration problem when primary PET images for the monitoring examinations are indexed for a patient after an operation and/or in the course of a different treatment and when, to reduce or avoid the radiation dose to be applied to the patient and for reasons of additional costs, it is desired to omit the respective CT acquisitions that would otherwise be generated simultaneously. A similar problem exists when a patient for whom an examination with a CT apparatus provides inducement for a further examination with PET is remitted to a clinic or hospital that also operates a CT/PET machine. It can wholly be assumed that the still-new dual-modality systems are not installed or are only installed to a limited extent in radiological institutes. Radiology and nuclear medicine are different profession directions, and normally only nuclear medicine institutes have authorization for the exposure with open radioactive substances such as, for example, radio-pharmaceuticals. The question exists as to whether and which compromises should be made for the application of one of the two modalities when both modalities are integrated in one apparatus. It is thus likely that the above-described double modality systems will not replace the use of apparatus that perform one or the other of the two individual modalities of the dual system.

The problem of an optimal image registration and fusion thus remains.

SUMMARY OF THE INVENTION

An object of the present invention is to provide a registration aid for medical images that can be connected in a reproducible manner with the patient with regard to selected body positions and on whom markings are located that are suitable for multimodal image registration, thus, for example, that appear both in a non-nuclear-medicine image and in a nuclear-medicine image.

The above object is achieved in accordance with the present invention by a registration aid that allows the contents of respective images obtained from an examination subject at separated points in time with two different imaging modalities to be brought into registration with each other, the registration aid having a carrier that is adapted to be reproducibly applied to the examination subject at the separated points in time, the carrier carrying at least one landmark provider that is applied to the examination subject at a defined spatial position, due to the application of the carrier to the patient. The landmark provider provides different landmarks that are respectively visible in the images obtained with the different imaging modalities, the different landmarks nevertheless having a fixed spatial relation to each other, thereby allowing registration of the contents of the respective images.

The carrier can be in the form of a belt or girdle that is worn by the patient and can be custom-designed for a particular patient to improve the reproducible positioning of the carrier on the patient, when the carrier has been removed from the patient and is then subsequently reapplied to the patient.

The carrier can carry multiple landmark providers.

The landmark provider or providers can each provide a landmark that is visible in a non-nuclear-medicine image, such as a CT image, and a landmark that is visible in a nuclear-medicine image, such as a PET image. In one embodiment, each landmark provider is composed of a hollow body that is visible as a cross-section in the CT image, with a radiation-permeable vessel inserted into the hollow body that is filled with a PET-specific radioactive substance, to produce a landmark in a PET image. In another embodiment, the landmark provider is in the form of a radiation-permeable tube or conduit or hose that is filled with a PET-specific radioactive substance, to produce a landmark in the PET image and the cross-section of the tube, conduit or hose is visible as a landmark in the CT image.

DESCRIPTION OF THE DRAWINGS

FIG. 2b shows components of a landmark provider in the embodiment of the registration aid shown in FIG. 2a.

FIG. 4a shows components of a further embodiment of a landmark provider suitable for use in the embodiment of the registration aid shown in FIG. 2a.

FIG. 4b shows components of another embodiment of a landmark provider suitable for use in the embodiment of the registration aid shown in FIG. 2a.

DESCRIPTION OF THE PREFERRED EMBODIMENTS

Figure 2A:
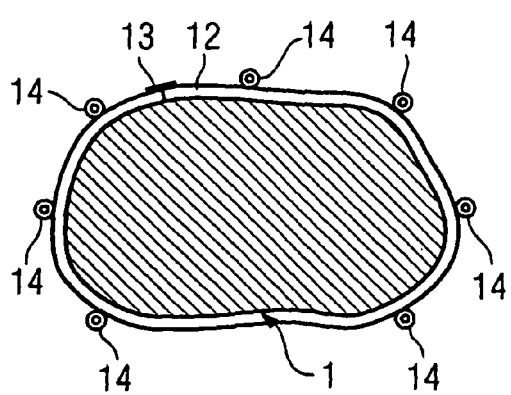
FIG. 2a illustrates a cross section of a registration aid, constructed in accordance with the present invention, applied to a patient in a first embodiment.
Figure 2B:
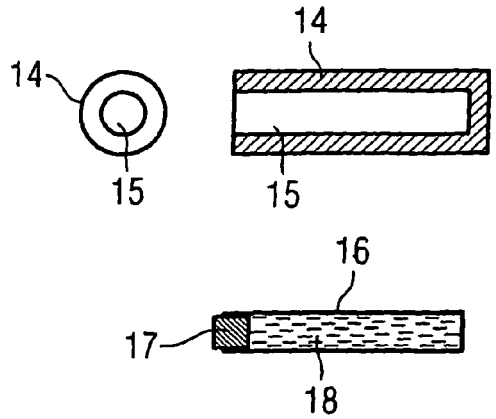

FIG. 2a shows that a girdle or belt is applied along the body periphery and the point of the cross-section to be imaged and is fastened with the clasp 13. Circular cylindrical hollow bodies 14 according to FIG. 2b are applied over the extent of the girdle 12, the hollow bodies 14 being composed of a material that shows well in a CT image. A CT acquisition then leads to an image according to FIG. 3a in which the hollow bodies 14 appear as landmarks 14'. The circular-cylindrical hollow bodies 14 are aligned essentially perpendicularly to the cross-section plane. Given a number of CT exposures of an acquisition process, a systematized inclination of the cylindrical hollow bodies 14 could be used to monitor and, if applicable, to correct the position of imaged cross-sections with regard to the system axis of the apparatus and to one another, in any case in the region of the length of the cylindrical hollow bodies 14 because these then appear spatially displaced in the images.

If the patient is directly transferred to a PET apparatus following the examination with CT, this occurs with the girdle 12 remaining worm, the girdle 12 optimally retains its position on the body of the patient due to suitable width and elasticity. Immediately before a PET examination, a circular-cylindrical vessel 16 is loaded with the fastener 17 that, due to being filled with a radioactive substance 18, emits a radiation suitable for its representation in the PET exposure, such that a PET image according to FIG. 3b is produced in which cylindrical vessels 16 located in the cylindrical hollow bodies 14 fastened on the girdle 12 appear as the landmarks 14". The hollow bodies 14 and the vessel 16 thus each constitute landmark providers. The landmark providers are composed of a material that is permeable for the radiation emitted by the substance 18.

Given a number of PET exposures of an acquisition process, the systematized inclination of the cylindrical hollow bodies 14 discussed above leads to a systematized inclination of the cylindrical vessels 16, which could be used to monitor and, if applicable, to correct the position of imaged cross-sections with regard to the system axis of the apparatus and to one another, in any case in the region of the length of the cylindrical vessels 16 because these then appear spatially displaced in the images. Because the systematized inclination of the cylindrical hollow bodies 14 also applies for the inserted cylindrical vessels 16, the discussed references also apply between CT exposures and PET exposures.

Figure 1A:
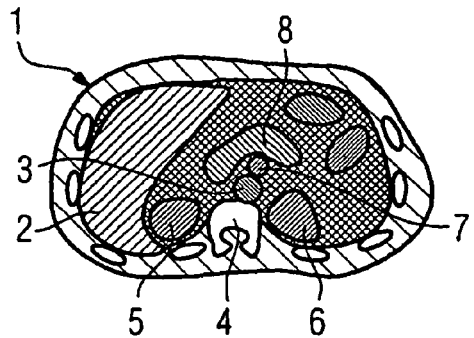
FIG. 1a, 1b, 1c and 1d, as explained above, illustrate the problem of providing registration between images respectively obtained with different imaging modalities.
Figure 1B:
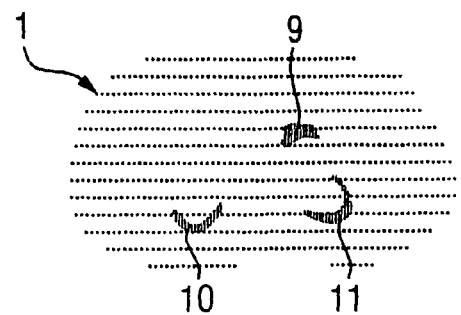
Figure 1C:
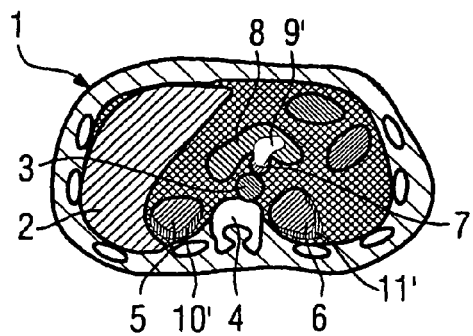
Figure 1D:
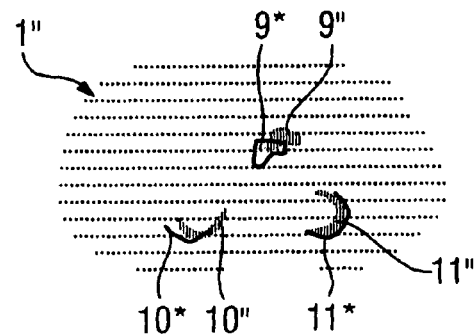
Figure 3A:
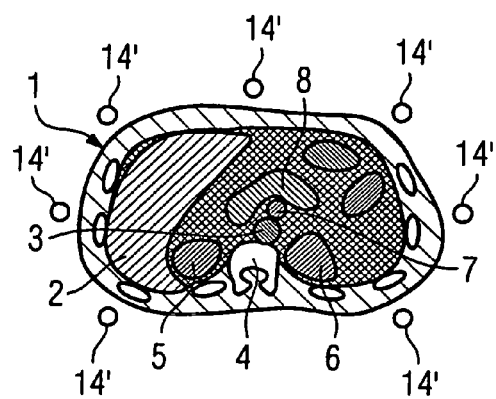
FIGS. 3a and 3b illustrate image registration of, as an example, a CT image and a PET image using the registration aid in accordance with the present invention.
Figure 3B:
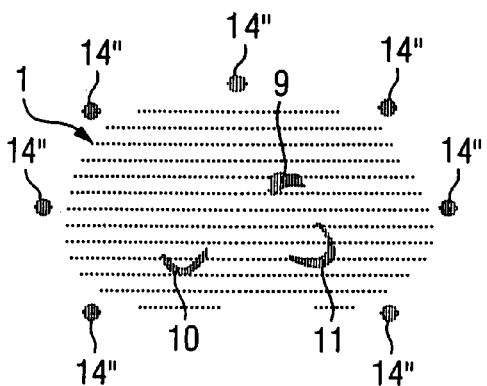

The center of a landmark 14' in FIG. 3*a* as well as the center of the landmark 14" associated with it in FIG. 3*b* both correspond to the center of the cross-section of the associated cylindrical hollow body 14. All landmarks 14" and 14" can now be used as a registration aid, whereby the registration simply has the object to bring the respective landmarks 14' and 14" associated with one another into congruence in a common coordinate system for both images by means of transformation measures discussed above. The use of enrichments of the radio-pharmaceutical in the non-target areas should not be foregone, as in, for example, the enhancement 10 and 11 according to FIG. 1*b* or (when organ displacements have occurred between the examinations with CT and PET) the adequate enhancements 10" and 11" according to FIG. 1*d* (which are all enhancements in the boundary regions of the kidneys 5 and 6 according to FIG. 1 or FIG. 3*a*).

The radiation-emitting cylindrical vessel 16 in FIG. 2*b* preferably is in the form of a hollow cylinder made of radiation-permeable material that, before the examination of the patient with the PET apparatus, is filled with a diluted preparation of the radio-pharmaceutical used in the examination.

The girdle 12 in FIG. 2*a* is initially a schematic representation of the mounting of the cylindrical hollow bodies 14. The girdle 12 can be designed such that the hollow bodies 14 are insertable into and removable from mountings attached to the girdle 12. The hollow bodies 14 do not have to be permanently connected with the girdle when, as long as they can be reproducibly inserted at the same position. During the CT examination, the hollow space 15 can also be filled with a fitting (solid) cylinder made from the same material as the hollow body 14, such that the landmarks 14' in FIG. 3*a* do not appear as an annulus but rather as a circle.

If the hollow bodies 14 can be reproducibly pulled out of or pushed into the girdle 12, given a transfer from an examination with CT to one with PET they can also be exchanged for the cylindrical vessels 16 filled with a radioactive substance 18 and sealed with a fastener 17 when these vessels 16 (for simplicity) have the same external shape as those of the hollow bodies 14. In this case, the hollow bodies 14 can also be executed as solid cylinders and would also not have to be composed of a material that is sufficiently permeable for the radiation emitted by the radioactive substance 18.

In one embodiment the girdle 12, is designed as a corset or bodice adapted to the patient body, which also offers the possibility to be reproducibly applied again with regard to body positions after intervening storage. It is also helpful to design the configuration of the corset fastener such that it can be protocolled for each selected adaptation. Such a reproducible corset offers not only the advantage of always being able to position the landmark providers 14 and 16 repeatedly at the same points on the periphery of the body cross-section, but rather could also (in furtherance of the support function of the girdle 12 due to its shape) facilitates bringing the inner organs into the same configuration in the cross-section to be represented as existed in preceding examinations. This applies regardless of which type of preceding examination was employed, whether (for example) CT or PET.

The circular-cylindrical hollow body 14 and the circular-cylindrical vessel 16 for the radioactive substances that are to be inserted therein can be designed with different embodiments. A conically-tapered hollow body 19 with a conically-tapering hollow space 20 can be used, as shown in FIG. 14*a*. Instead of the vessel 16, the associated vessel 21 sealed with a fastener 22 is adapted in shape to the conically-tapering hollow space 19. Landmark providers assembled in such a manner and with known dimensions are advantageous, such that using the landmark dimensions it can be established in the images whether the images of both modalities also show the same body-cross-section or whether, if applicable, images of cross-sections at another point are to be selected, namely for cross-sections at another point along the patient body axis (in any case within the range in which the landmark also extend). This is particularly important when the images of a number of image pairs matching one another are registered along the body axis. The registration of images one after the other on the body axis plays a role for the transition of the two-dimensional registration, discussed here, to a three-dimensional registration.

Figure 4A:
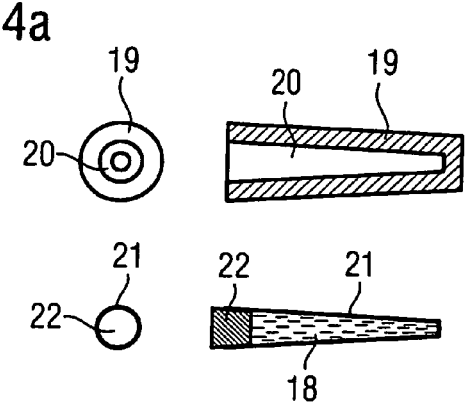
Figure 4B:
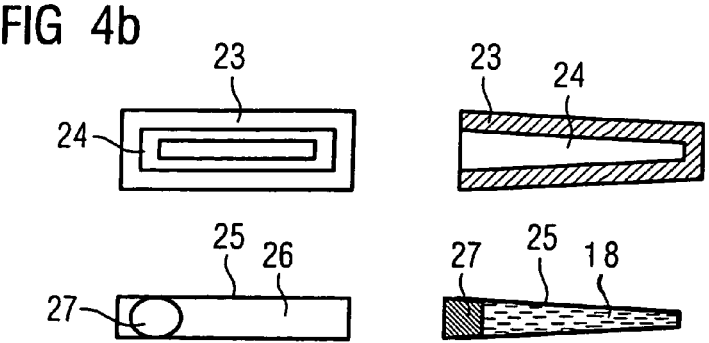

The same applies for the case that, instead of a circular cross-section, the hollow body 14 and the associated vessel 16 or the hollow body 19 and the associated vessel 21 have an elliptical or rectangular cross-section that is suitable as a registration aid with a defined center point in the same manner as a circular cross-section. FIG. 4*b* shows such an arrangement for a rectangular cross-section with the hollow body 23, having a hollow space 24, a vessel 25 with the radioactive filling 18 that tapers along its length with regard to the small axis of the rectangular cross-section and with a sealing plate 26 for this vessel 25 with the fill hole sealed by a fastener 27.

The hollow bodies 14, 19 and 23 need not have a symmetrical cross-sections (such as a circular, elliptical or rectangular cross-section). The same is true for the vessels 16, 21 and 23. The cross-section of a prism is possible when only one topologically-identical point can determined in a simple manner in both associated landmarks, thus in the CT image and in the PET image. Moreover, the cross-section of the hollow bodies 14, 19 and 23 do not have to have the same shape as their hollow spaces 15, 20 and 24; the latter would merely have to coincide with the cross-sections of the vessels 16, 21 and 25.

Given departure from the shape of a cylinder, cone, truncated cone or prism for the landmark provider (hollow bodies according to 14, 19 and 23 and the associated vessels 16, 21 and 25), it is necessary for the vessels to have a smooth jacket or a conical, frustrum-shapes or prism-shaped jacket that continuously changes in the axial direction along the inner wall of the hollow bodies and along the outer wall of the vessels, to allow insertion into the hollow body from the front side with positive fit.

The necessity is avoided by forming the hollow body from two half-shells, and thus a vessel fitting its shape could be correspondingly inserted into it. The shape of the vessel is then largely independent of the shape of the inner space of the hollow body in which it is to be inserted.

Freedom from a particular shape is facilitated if a coding is associated were connected with the shape, which coding allows the position of the cross-sections along the landmark providers to be seen on the landmarks in the cross-section images. Such a coding is also possible for all other previously discussed landmark providers, namely by the application of engravings or grooves, for example on the outer jacket of the hollow bodies with respective equivalence on the outside of the hollow vessels filled with radioactive substance 18.

Freedom with regard to the shape is also facilitated if solid bodies are used instead of the hollow bodies 14, 19 and 23. The solid bodies are inserted into mounts located on the girdle 12 and, given the transfer of the examination with CT to the examination with PET, are exchanged for identically-shaped vessels filled with the required radioactive substance.

Figure 5A:
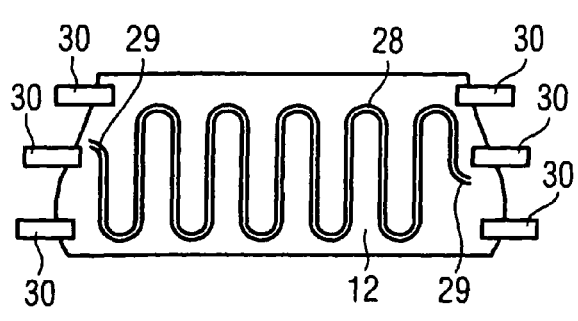
FIGS. 5a, 5b and 5c, respectively, show different versions of a further embodiment of a registration aid in accordance with the present invention.

Another approach for an embodiment of the hollow bodies 14, 19 and 23 is a flexible tube or hose 28 with ends 29 that (according to FIG. 5a and, b) are permanently connected with the girdle 12 or the corset with the fastener parts 30, and that are filled with the imaging radioactive fluid before or during the examination with the PET apparatus. In the CT acquisitions, the wall of the tube 28 generates the landmarks; in the PET acquisitions, the radioactive fluid inside said tube 28 generates the landmarks. In such an arrangement, the required radioactive substance can presumably be introduced into and extracted more simply and quickly than, for example, a series of hollow bodies 14, 19 and 23 and the associated vessels 16, 21 and 25. This is also advantageous for a PET examination when it is only desired to introduce the landmark by filling of the flexible tube or hose 28 with radioactive substance when the desired imaging effect of the radio-pharmaceutical administered to the patient occurs with a delay. The flexible tube 28 can also be incorporated into the girdle 12 because it would be to be filled and emptied via its ends 29.

Figure 5B:
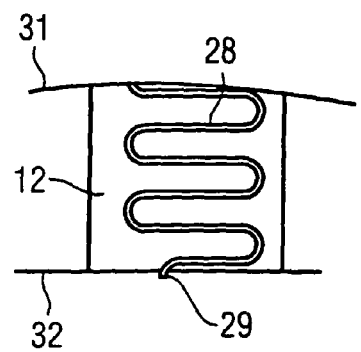
Figure 5C:
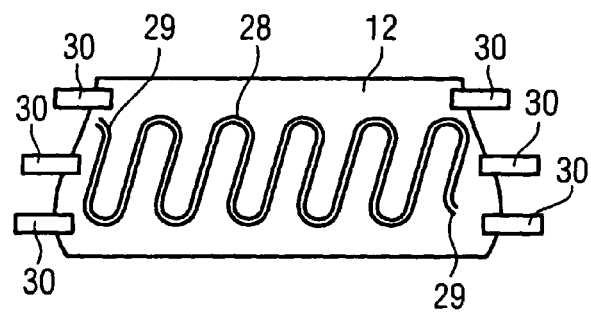

The flexible tube or the hose 28 on the girdle 12 or the corset or bodice can also have a different contour for that shown in FIG. 5c in which the tube 28 proceeds in a serpentine manner at an angle over the girdle 12. Individually, the landmarks mapped in the cross-section images for this example would not be suitable for the registration, but due to their position in the image also indicate the location of the body cross-section in the region of the landmark provider, thus of the tube 28 on the girdle 12.

The position of an applied girdle 12 or corresponding corset should remain unchanged and be optimally reproducible given repeated removal and application. Auxiliary means for securing or reproducing the precise positioning can be markers on the patient body that, for example, are marked beforehand or identically applied on the skin of the patient by sighting holes or hole templates in the girdle 12, whereby upon reapplication of the girdle 12 these sighting holes are brought into congruence again with the markings to monitor the correct positioning.

The above discussion has been in the context of cross-sections on the body trunk. For examination head, a similar consideration apply, but instead of the girdle 12 a cap (for example in the form of a leather motorcycle cap) would be suitable as a carrier of the landmark providers, in particular with regard to the reproducibility of their previous positions upon reapplication.

Figure 6:
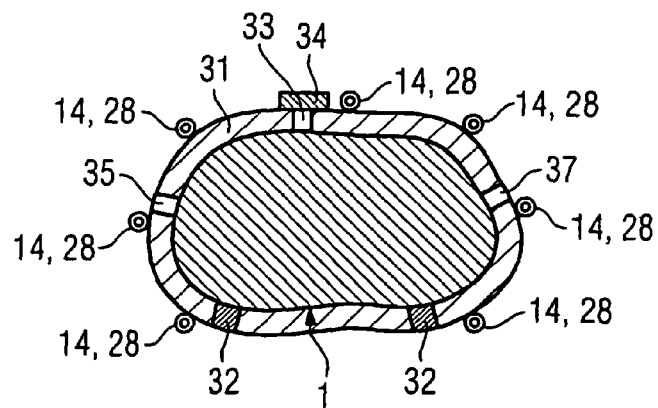
FIG. 6 shows a sectional view of another embodiment of a registration aid in accordance with the invention applied to a patient, wherein the registration aid is composed of multiple, joined parts forming a shell.

In the case of particularly high requirements for the reproducibility of the position of the girdle 12 as a carrier of the landmark providers on the body, the girdle 12 can be designed as a body shell 31 according to FIG. 6, that is adapted to the patient. In such a body shell the patient lies in a pre-formed but still plastic, deformable shell having a shell wall in which, if applicable, a grid or meshwork can be incorporated that is made from plastic that has not yet hardened to adapt to the patient, or from another suitable material. In the still plastic, deformable state, this shell is conformed to the patient and then hardens in this state. So that this shell 31 can be stored again for later repeated use, it is provided with one or more flexible joints, hinges articulations 32. The opening gap 33 is closed with a sealing mechanism 34 such as a Velcro® fastener. The shell 31 can be equipped with landmark providers according to the hollow bodies 14, 19 and 23 and the associated vessels 16, 21 and 25 according to FIG. 2a through 4b, and with a flexible tube 28 according to FIGS. 5a through 5c, whereby the landmark providers rest on the shell 31 or are incorporated therein. For the representation in FIG. 6, the tube 28 was selected as a landmark provider; sighting 35 holes or hole templates as already described in connection with the girdle 12 have also been noted as aids (as sighting holes 35 [sic]) for position marking before the storage of the shell 31 and for monitoring of the shell position after reapplication. This body shell 31 accompanies a patient, for example during the time period of required monitoring examinations after treatment or treatments, in order, for example, to track changes in size, shape and/or position of a pathology.

The previously discussed considerations for bimodal systems (here for CT in combination with one of the nuclear medicine modalities PET or SPECT) can be analogously transferred to a bimodal system in which the imaging modality MRT occurs in place of CT. For the hollow bodies 14, 19 and 23 and, if applicable, the associated hollow vessels 16, 21 and 25 according to FIGS. 2a through 4b, or for the flexible tube 28 according to FIGS. 5a through 5c and FIG. 6, a material is used that shows up well in an MRT image and is sufficiently permeable for the radiation emanating from the radioactive material used for the landmark provision in the PET or SPECT image on the other hand.

The use of a registration aid could be considered for the case of the bimodality CT/MRT, but in general a registration would not be needed in that context, because CT and MRT both comprehensively show the morphology of the organs. Nevertheless, a registration aid of the type described above may be useful in special cases.

The combination of an ultrasound slice image with an image according to the methods cited above would likewise be possible in principle. Instead of a girdle 12, for example, a flat gel-filled or fluid-filled foil conduit would be suitable as a carrier. Such a registration aid would be only of limited assistance in this context, however, because, in an ultrasound image apparatus, body cross-sections that are required and suitable for a diagnosis are produced by the examining doctor by directing the scanner head, and such body cross-sections normally are not axial (with regard to the longitudinal axis of the patient body), which is why in general a fixed reference system (provided by the apparatus) for the image is not needed with this modality, (unlike the other cited modalities).

Ultrasound imaging (which is normally a moving picture or film in which the temporal changes of organ structures are thus shown) nevertheless offers a new aspect for consideration with the other bimodalities. For example, the temporal changes of the radiation of a disease source shown in a nuclear diagnostic image could be superimposed on a static CT image.

Monomodal image registration and fusion was discussed above as an example to reliably track (by means of CT) a disease or healing progress for a soft tissue disease in the skull. The cranial bone offers a reliable reference system for the registration of a reference exposure showing the initial situation and following exposures. For body parts that have no fixed frame (as the cranial bone provides for the skull) that can serve as a reference system for the registration of images generated in temporal sequence, the registration is difficult even in a monomodal case, for example due to a displacement of internal organs. The multimodal (in particular bimodal) registration aids described herein can also be used for a monomodal registration, whereby these are applied for just one modality even though they are designed for bimodality. They can also be designed from the outset for only one modality, as would be the case for CT image. Such a registration aid (for example as shown in FIG. 2) is formed by the girdle 12 with hollow bodies 14 (or their continuations) applied on its extent, which hollow bodies 14 are composed of a material that shows up well in a CT image.

Although modifications and changes may be suggested by those skilled in the art, it is the intention of the inventors to embody within the patent warranted hereon all changes and modifications as reasonably and properly come within the scope of their contribution to the art.

I claim as my invention:

1. A registration aid for medical images obtained from an examination subject respectively with different imaging modalities at separated points in time, said registration aid comprising:
    a carrier adapted to be reproducibly applied to an examination subject at separated points in time at a substantially identical position on the examination subject at each of the separated points in time; and
    at least one landmark provider carried by said carrier, said landmark provider providing a first landmark visible in a first of said imaging modalities and a second landmark, different from said first landmark, visible in a second of said imaging modalities, said landmark provider providing said first and second landmarks with a fixed spatial relation relative to each other to allow contents of an image obtained with said first of said imaging modalities to be brought into registration with contents of an image obtained with said second of said imaging modalities, with said carrier being applied to the examination subject while each of said images is obtained.

2. A registration aid as claimed in claim 1, wherein said carrier comprises an article adapted to be worn around a trunk region of the examination subject.

3. A registration aid as claimed in claim 2, wherein said article is a shell that is custom-fit to the trunk region of the examination subject.

4. A registration aid as claimed in claim 3, wherein said shell is comprised of multiple, connected shell parts.

5. A registration aid as claimed in claim 4 comprising a plurality of articulations connecting said multiple shell parts to each other to facilitate application and removal of said carrier.

6. A registration aid as claimed in claim 1, wherein said carrier comprises a sighting hole proceeding therethrough, allowing said carrier to be applied to the examination subject with a mark at a predetermined location on the examination subject being visible through the citing hole.

7. A registration aid as claimed in claim 1, wherein said first landmark provided by said landmark provider is visible in a non-nuclear-medicine image and wherein said second landmark provided by said landmark provider is visible in a nuclear medicine image.

8. A registration aid as claimed in claim 7, wherein said first landmark is visible in an image selected from the group consisting of magnetic resonance images and computed tomography images and wherein said second landmark is visible in images selected from the group consisting of PET images and SPECT images.

9. A registration aid as claimed in claim 7, wherein said at least one landmark provider comprises a hollow body having an opening therein giving said hollow body a cross-section that is visible in said non-nuclear-medicine image, and a vessel disposed in said opening of said hollow body, said vessel containing a radioactive substance that is specific for said nuclear medicine image, said holder being permeable to radiation emitted by said radioactive substance.

10. A registration aid as claimed in claim 9 wherein said opening in said holder tapers toward one end of said holder, to cause said cross-section of said holder to differ in said non-nuclear medicine image, depending on where said non-nuclear-medicine image is obtained along a depth of said opening.

11. A registration aid as claimed in claim 7, wherein said at least one landmark provider comprises an elongate tube attached along a substantial extent of said carrier, said elongate tube having a cross-section that is visible in said non-nuclear-medicine image and containing a radioactive substance that emits radiation specific for said nuclear medicine image, said tube being permeable to said radiation, said tube defining a non-zero angle with respect to a longitudinal axis of the examination subject when said carrier is applied to the examination subject.

12. A registration aid as claimed in claim 11, wherein a tube has a serpentine configuration.

* * * * *